(12) United States Patent
Driver et al.

(10) Patent No.: US 7,732,651 B2
(45) Date of Patent: Jun. 8, 2010

(54) METHOD OF MAKING AN ALKYLATED AROMOATIC USING ACIDIC IONIC LIQUID CATALYST

(75) Inventors: Michael Driver, San Francisco, CA (US); Curt B. Campbell, Hercules, CA (US); Thomas V. Harris, Benicia, CA (US)

(73) Assignee: Chevron Oronite Company, LLC, San Ramon, CA (US)

( * ) Notice: Subject to any disclaimer, the term of this patent is extended or adjusted under 35 U.S.C. 154(b) by 663 days.

(21) Appl. No.: 11/445,561

(22) Filed: Jun. 1, 2006

(65) Prior Publication Data

US 2007/0282143 A1 Dec. 6, 2007

(51) Int. Cl.
*C07C 2/70* (2006.01)
*C07C 2/26* (2006.01)

(52) U.S. Cl. .................. 585/323; 585/455; 585/456; 585/521; 585/511

(58) Field of Classification Search .................. 585/323, 585/455, 456, 521, 511
See application file for complete search history.

(56) References Cited

U.S. PATENT DOCUMENTS

| | | | |
|---|---|---|---|
| 4,503,277 A | 3/1985 | Himes | |
| 5,026,933 A * | 6/1991 | Blain et al. ..................... | 585/7 |
| 5,304,615 A | 4/1994 | Ambler et al. | |
| 5,502,018 A | 3/1996 | Chauvin et al. | |
| 5,550,304 A | 8/1996 | Chauvin et al. | |
| 5,731,101 A | 3/1998 | Sherif et al. | |
| 5,994,602 A | 11/1999 | Abdul-Sada et al. | |

FOREIGN PATENT DOCUMENTS

| | | |
|---|---|---|
| EP | 0 791 643 A1 | 8/1997 |
| EP | 0 558 187 A1 | 1/2003 |
| WO | WO 95/21871 | 8/1995 |
| WO | WO 95/21872 | 8/1995 |
| WO | WO 96/18459 | 6/1996 |
| WO | WO 98/50153 | 11/1998 |
| WO | WO 00/32658 | 6/2000 |

OTHER PUBLICATIONS

B. Ellis, W. Keim and P. Wasserscheid, Linear dimerisation of but-1-ene in biphasic mode using buffered chloroaluminate ionic liquid solvents, 1999, 337-338, Chem. Commun.
J.D. Holbrey, K.R. Seddon, Ionic Liquids, 1999, 223-236, Clean Products and Processes 1, Springer-Verlag 1999.
Helene Olivier, Recent developments in the use of non-aqueous ionic liquids fro two-phase catalysis, 1999, 285-289, Journal of Molecular Catalysis A; Chemical 146. Institut Francais de Petrole, France.
Yves Chauvin, Helene Oliver-Bourbigou, Nonaqueous ionic liquids as reacation solvents, Chem. Tech, 1995, 26-31, Enabling Science.

* cited by examiner

*Primary Examiner*—Thuan Dinh Dang
(74) *Attorney, Agent, or Firm*—Josetta I. Jones, Esq; M. Carmen & Associates, PLLC

(57) ABSTRACT

A process for alkylating an aromatic compound containing no hydroxyl groups comprising reacting at least one non-hydroxyl containing aromatic compound with at least one olefinic oligomer in the presence of an acidic ionic liquid catalyst, wherein the olefinic oligomer has a carbon range of from about $C_{12}$ to about $C_{70}$ and is synthesized by oligomerizing at least one monoolefin monomer in the presence of an acidic ionic liquid catalyst.

22 Claims, No Drawings

METHOD OF MAKING AN ALKYLATED AROMOATIC USING ACIDIC IONIC LIQUID CATALYST

FIELD OF THE INVENTION

The present invention is directed to a process for alkylating an aromatic compound containing no hydroxyl groups by reacting a non-hydroxyl containing aromatic compound with an olefinic oligomer in the presence of an acidic ionic liquid catalyst.

BACKGROUND OF THE INVENTION

It is well known to catalyze the alkylation of aromatics with a variety of Lewis or Bronsted acid catalysts. Typical commercial catalysts include phosphoric acid/kieselguhr, aluminum halides, boron trifluoride, antimony chloride, stannic chloride, zinc chloride, onium poly(hydrogen fluoride), hydrogen fluoride, acidic ionic exchange resins, acidic clays, synthetic or natural zeolites, and solid acids such as amorphous silica-alumina. Alkylation with lower molecular weight olefins, such as propylene, can be carried out in the liquid or vapor phase. For alkylations with higher olefins, such as $C_{16+}$ olefins, the alkylations are done in the liquid phase, often in the presence of hydrogen fluoride. Alkylation of benzene with higher olefins may be difficult, and typically requires hydrogen fluoride treatment. Such a process is disclosed by Himes in U.S. Pat. No. 4,503,277, entitled "HF Regeneration in Aromatic Hydrocarbon Alkylation Process," which is hereby incorporated by reference for all purposes.

One problem with using acids, such as hydrogen fluoride, is that these acids are extremely corrosive, thus requiring special handling and equipment. Furthermore, the use of these acids might involve environmental problems. Another problem is that the use of these acids gives less desirable control of the precise chemical composition of the product.

DESCRIPTION OF THE RELATED ART

Ambler et al., U.S. Pat. No. 5,304,615 discloses polymerizing an olefinic feedstock comprising one or more of butene-1, butene-2 and iso-butene by bringing the feedstock into contact with an ionic liquid.

Abdul-Sada et al., U.S. Pat. No. 5,994,602 discloses a process for the alkylation of aromatics by reacting an aromatic hydrocarbon with an olefin in the presence of an ionic liquid.

SUMMARY OF THE INVENTION

In its broadest embodiment, the present invention is directed to a non-hydroxyl containing alkyl aromatic compound wherein the alkyl substituent is derived from an olefinic oligomer having a carbon range of from about $C_{12}$ to about $C_{70}$ and wherein the oligomer is prepared by oligomerizing at least one monoolefin monomer in the presence of an acidic ionic liquid catalyst.

In another embodiment, the present invention is directed to a process for alkylating an aromatic compound containing no hydroxyl groups comprising reacting at least one non-hydroxyl containing aromatic compound with at least one olefinic oligomer in the presence of an acidic ionic liquid catalyst, wherein the olefinic oligomer has a carbon range of from about $C_{12}$ to about $C_{70}$ and is synthesized by oligomerizing at least one monoolefin in the presence of an acidic ionic liquid catalyst.

DETAILED DESCRIPTION OF THE INVENTION

While the invention is susceptible to various modifications and alternative forms, specific embodiments thereof are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

Definitions

Olefins—The term "olefins" refers to a class of unsaturated aliphatic hydrocarbons having one or more carbon-carbon double bonds, obtained by a number of processes. The term "monoolefin" refers to olefins having one double bond. Alpha olefins are also included in the definition of olefins.

Alpha Olefins—The term "alpha olefins" refers to olefins that have a double bond between the first and second carbon atoms and are particularly reactive. Examples are 1-octene and 1-octadecene, which are used as the starting point for medium-biodegradable surfactants. Linear and branched olefins are also included in the definition of olefins.

Linear Olefins—The term "linear olefins," which include normal alpha olefins and linear alpha olefins, refers to olefins which are straight chain, non-branched hydrocarbons with at least one carbon-carbon double bond present in the chain.

Double-Bond Isomerized Linear Olefins—The term "double-bond isomerized linear olefins" refers to a class of linear olefins comprising more than 5% of olefins in which the carbon-carbon double bond is not terminal (i.e., the double bond is not located between the first and second carbon atoms of the chain).

Partially Branched Linear Olefins—The term "partially branched linear olefins" refers to a class of linear olefins comprising less than one alkyl branch per straight chain containing the double bond, wherein the alkyl branch may be a methyl group or higher. Partially branched linear olefins may also contain double-bond isomerized olefins.

Branched Olefins—The term "branched olefins" refers to a class of olefins comprising one or more alkyl branches per linear straight chain containing the double bond, wherein the alkyl branch may be a methyl group or higher.

Non-Hydroxyl Containing Aromatic Compounds—The term "non-hydroxyl containing aromatic compounds" refers to aromatic compounds that do not have any hydroxyl groups either on the aromatic ring or on any substituent group(s).

Unsubstituted Aromatic Compounds—The term "unsubstituted compounds" refers to aromatic compounds that do not have any substituents attached to the aromatic ring(s). These compounds may be monocyclic, bicyclic or polycyclic. Examples of such compounds include, but are not limited to, benzene, naphthalene and the like.

Monosubstituted Aromatic Compounds—The term "monosubstituted compounds" refers to aromatic compounds that have one substituent attached to the aromatic ring. These compounds may be monocyclic, bicyclic or polycyclic. Examples of such compounds include, but are not limited to, aromatic compounds with one of the following substituents: —OR, —R, —X, —NH$_2$, —NHR or —NR$_2$ and the like, wherein R is an alkyl group and X is a halide.

Disubstituted Aromatic Compounds—The term "disubstituted compounds" refers to aromatic compounds that have two substituents attached to the aromatic ring(s). The aromatic compounds may be monocyclic, bicyclic or polycyclic. Examples of such compounds include, but are not limited to, aromatic compounds with two substituents selected from the following: —OR, —R, —X, —NH$_2$, —NHR or —NR$_2$ and the like, wherein R is an alkyl group and X is a halide.

Bronsted Acid—The term "Bronsted Acid" refers to a Lowry-Bronsted acid which is defined as a substance that gives up a proton. The strength of this acid depends upon its tendency to give up a proton. Substances that readily give up protons are typically strong acids. Sulfuric acid and hydrogen chloride are examples of strong Bronsted acids.

One embodiment of the present invention is a process for preparing an alkylated aromatic compound, wherein said process comprises reacting at least one aromatic compound with an olefinic oligomer, wherein the olefinic oligomer has a molecular weight of from about 160 to about 850 and is synthesized by oligomerizing an olefin in the presence of an acidic ionic liquid catalyst.

Aromatic Compound

At least one non-hydroxyl containing aromatic compound may be used for the alkylation reaction in the present invention. Specifically, the aromatic compound does not contain any hydroxyl groups either directly attached to the aromatic ring or on any of the substituents that are attached to the aromatic ring. Preferably the at least one aromatic compound comprises at least one of monocyclic aromatics, such as benzene, toluene, xylene—including all isomers (i.e., meta-, ortho- and para-), cumene or mixtures thereof. The at least one aromatic compound may also comprise bi-cyclic and poly-cyclic aromatic compounds, such as naphthalenes.

The aromatic compound may be an unsubstituted aromatic compound, a monosubstituted compound, and/or a disubstituted compound.

Sources of Aromatic Compound

The at least one aromatic compound employed in the present invention is prepared by methods that are well known in the art.

Olefinic Oligomer

The olefinic oligomer employed in this invention may be synthesized by reacting a low molecular weight monoolefin monomer in the presence of an acidic ionic liquid. The olefinic oligomer has a carbon range of from about C$_{12}$ to C$_{70}$. Preferably, the olefinic oligomer is a propylene oligomer.

Monoolefin Monomer

The low molecular weight monoolefin monomer employed in this invention may be linear, isomerized linear, branched or partially branched linear olefins, or a mixture thereof.

The monoolefins may be derived from a variety of sources. Such sources include the normal alpha olefins from a normal alpha olefin process or an olefin metathesis process. Another source from which the olefins may be derived is through cracking of petroleum or Fischer-Tropsch wax. The Fischer-Tropsch wax may be hydrotreated prior to cracking. Other commercial sources include olefins derived from paraffin dehydrogenation, methanol-to-olefin processes (methanol cracker), and the like. Another source of olefins may be refinery olefins, such as those derived from a fluid catalytic cracker (FCC) unit. Another source of olefins may be those derived from Fischer-Tropsch synthesis.

The monoolefins may also be substituted with other functional groups, such as carboxylic acid groups, heteroatoms, and the like, provided that such groups do not react with the acidic ionic liquid catalyst.

Isomerized Normal Alpha Olefin Monomer

In one embodiment of the present invention the monoolefin employed is a normal alpha olefin. The normal alpha olefins may be isomerized using at least one of two types of acidic catalysts, solid or liquid. A solid catalyst preferably has at least one metal oxide and an average pore size of less than 5.5 angstroms. More preferably, the solid catalyst is a molecular sieve with a one-dimensional pore system, such as SM-3, MAPO-11, SAPO-11, SSZ-32, ZSM-23, MAPO-39, SAPO-39, ZSM-22 or SSZ-20. Other possible acidic solid catalysts useful for isomerization include ZSM-35, SUZ-4, NU-23, NU-87 and natural or synthetic ferrierites. These molecular sieves are well known in the art and are discussed in Rosemarie Szostak's Handbook of Molecular Sieves (New York, Van Nostrand Reinhold, 1992) which is herein incorporated by reference for all purposes. A liquid type of isomerization catalyst that can be used is iron pentacarbonyl (Fe(CO)$_5$).

The process for isomerization of normal alpha olefins may be carried out in batch or continuous mode. The process temperatures may range from about 50° C. to about 250° C. In the batch mode, a typical method used is a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at least 150° C. under vacuum or flowing inert, dry gas. After activation, the temperature of the isomerization catalyst is adjusted to the desired reaction temperature and a flow of the olefin is introduced into the reactor. The reactor effluent containing the partially-branched, isomerized olefins is collected. The resulting partially-branched, isomerized olefins contain a different olefin distribution (i.e., alpha olefin, beta olefin; internal olefin, tri-substituted olefin, and vinylidene olefin) and branching content that the unisomerized olefin and conditions are selected in order to obtain the desired olefin distribution and the degree of branching.

Preferably, the monoolefin monomer is propylene, butene, isobutylene, pentene or mixtures thereof. More preferred, the monoolefin monomer is propylene. Typically, the monoolefin monomer has a carbon range of from about C$_2$-C$_{10}$. Preferably, the monoolefin monomer has a carbon range of from about C$_3$-C$_5$.

Acidic Ionic Liquid Catalyst

The acidic ionic liquid catalyst is composed of at least two components which form a complex. The acidic ionic liquid catalyst in either the alkylation reaction or the olefin oligomerization process independently comprises a first component and a second component. The first component of the catalyst will typically comprise a Lewis Acidic compound selected from components such as Lewis Acidic compounds of Group 13 metals, including aluminum halides, alkyl aluminum halide, gallium halide, and alkyl gallium halide (see International Union of Pure and Applied Chemistry (IUPAC), version3, October 2005, for Group 13 metals of the periodic table). Other Lewis Acidic compounds besides those of Group 13 metals may also be used. Especially preferred for the first component is aluminum halide or alkyl aluminum halide. In particular, aluminum trichloride may be used as the first component for preparing the catalyst used in practicing the present invention.

The second component making up the ionic liquid catalyst is an organic salt or mixture of salts. These salts may be characterized by the general formula Q$^+$A$^-$, wherein Q$^+$ is an ammonium, phosphonium, boronium, iodonium, or sulfonium cation and A$^-$ is a negatively charged ion such as Cl$^-$, Br$^-$, ClO$_4^-$, NO$_3^-$, BF$_4^-$, BCl$_4^-$, PF$_6^-$, SbF$_6^-$, AlCl$_4^-$, ArF$_6^-$, TaF$_6^-$, CuCl$_2^-$, FeCl$_3^-$, SO$_3$CF$_3$—, SO$_3$C$_7^-$, and 3-sulfurtrioxyphenyl. Preferred for use as the second component are those quaternary ammonium halides containing one or more alkyl moieties having from about 1 to about 9 carbon atoms, such as, for example, trimethylamine hydrochloride, methyltributylammonium, and 1-butylpyridinium, or hydrocarbyl substituted imidazolium halides, such as for example, 1-ethyl-3-methyl-imidazolium chloride.

The presence of the first component should give the ionic liquid a Lewis or Franklin acidic character. Generally, the greater the mole ratio of the first component is to the second component, the greater the acidity of the ionic liquid mixture. When aluminum trichloride and trimethylamine hydrochloride are used as the first and second components, respectively, of the acidic ionic liquid catalyst, they preferably will be present in a mole ratio of from greater than about 1:1 to about 2:1.

Optionally, the acidic ionic liquid catalyst may comprise a third component. Preferably, the third component is a Bronsted acid. The Bronsted acid comprises hydrochloric acid (HCl), hydrobromic acid (HBr), trifluoromethanesulfonic acid, benzoic acid, para-toluene sulfonic acid, sulfuric acid and the like.

Preparation of Olefinic Oligomer

The olefinic oligomers employed in the present invention are synthesized by oligomerizing a low molecular weight monoolefin monomer in the presence of an acidic ionic liquid. Preferably the olefinic oligomer is selected from a propylene oligomer, a butene oligomer, an isobutylene oligomer, a pentene oligomer and mixtures thereof. Preferably, the olefinic oligomer is a propylene oligomer which is synthesized by oligomerizing propylene or isopropylene in the presence of an acidic ionic liquid. Preferably, the olefinic oligomer has a carbon range of from about 12 to about 60.

The olefin oligomer may be prepared by reacting the monoolefin monomer with the acidic ionic liquid catalyst, as described herein, in a continuous, batch or semi-batch reaction process at from about −20° C. to about 100° C. and a pressure of atmospheric pressure to about 1000 psig. These process conditions are not limiting. Optimization of process conditions in the oligomerization of the olefin is within the scope of this invention.

Process for Preparing Alkylated Aromatic Compound

The alkylation process is carried out by charging a hydrocarbon feed comprising an aromatic compound or a mixture of aromatic compounds, an olefinic oligomer and an acidic ionic liquid catalyst to a reaction zone in which agitation is maintained. The acidic ionic liquid catalyst employed in the alkylation process may or may not be the same acidic ionic liquid catalyst employed in the olefinic oligomerization process. The resulting reaction mixture, which comprises the aromatic compound, the olefinic oligomer, and the acidic ionic liquid, is held in the alkylation zone under alkylation conditions for a time sufficient to allow substantial conversion (i.e., at least 80 mole % of the olefin has reacted) of the olefin to an aromatic alkylate. After a desired time, the reaction mixture is removed from the alkylation zone and fed to a liquid-liquid separator to allow hydrocarbon products to separate from the acidic ionic liquid catalyst. The acidic ionic liquid catalyst may be recycled to the reactor in a closed loop cycle. The hydrocarbon product is further treated to remove excess un-reacted aromatic compounds and optionally olefinic compounds from the desired alkylate product. The excess aromatic compounds are also recycled to the reactor.

Many types of reactor configurations may be used for the reactor zone. These include, but are not limited to, batch and continuous stirred tank reactors, reactor riser configurations, ebulating bed reactors, and other reactor configurations that are well known in the art. Many such reactors are known to those skilled in the art and are suitable for the alkylation reaction. Agitation is critical for the alkylation reaction and can be provided by rotating impellers, with or without baffles, static mixers, kinetic mixing in risers, or any other agitation devices that are well known in the art.

The alkylation process may be carried out at temperatures from about −10° C. to about 100° C. The process is carried out under sufficient pressure that a substantial portion of the feed components remain in the liquid phase. Typically, a pressure of 0 to 1000 psig is satisfactory to maintain feed and products in the liquid phase.

The at least one aromatic compound or mixture of aromatic compounds and the olefinic oligomer may be injected separately into the reaction zone or may be mixed prior to injection. Both single and multiple reaction zones may be used with the injection of the aromatic compounds and the olefinic oligomer into one, several, or all reaction zones. The reaction zones need not be maintained at the same process conditions.

The charge mole ratio of the aromatic compound to the olefinic oligomer may range from about 0.5:1 to 100:1.

The alkylation process may be carried out in a batch or continuous process. The acidic ionic liquid catalyst may be recycled when used in a continuous process or batch process.

The olefinic oligomerization and alkylation processes may also take place in two separate reactors that are located in series. In the first reactor, the olefinic oligomerization takes place in accordance with the process steps described herein. The olefinic oligomerized product is then fed to a second reactor, wherein the alkylation process takes place in accordance with the process steps described herein.

The catalyst(s) used to make the olefinic oligomer and in the alkylation process may be recycled.

The product of the above-described olefin oligomerization and alkylation reactions is the non-hydroxyl containing alkylated aromatic compound herein.

Accordingly, another embodiment of the present invention is a non-hydroxyl containing alkylated aromatic compound wherein the alkyl substituent is derived from an olefinic oligomer having a carbon range of from about $C_{12}$ to $C_{70}$ and wherein the oligomer is prepared by oligomerizing at least one monoolefin monomer in the presence of an acidic ionic liquid catalyst.

Other embodiments will be obvious to those skilled in the art.

The following examples are presented to illustrate specific embodiments of this invention and are not to be construed in any way as limiting the scope of the invention.

EXAMPLES

Example 1

Preparation of Tri-methyltributylammonium Chloroaluminate Ionic Liquid Catalyst

Anhydrous aluminum trichloride and methyltributylammonium chloride were dried overnight under vacuum at 100° C.

The preparation of the ionic liquid catalyst was carried out in a dry box. 550.6 grams of methyltributylammonium chloride was added to a beaker which was equipped with a magnetic stirring bar. 622.7 grams of anhydrous aluminum chloride was added to a second beaker. With the magnetic stirred activated, small portions of the solid aluminum chloride were slowly added to the beaker of methyltributylammonium chloride. As aluminum chloride was added, the heat of the reaction rose and the reaction mixture turned "pasty" and then turned partially liquid. The rate of addition of aluminum chloride was slowed to moderate the temperature increase in the beaker. As more aluminum chloride was added, more liquid was formed and eventually the reaction mixture began to stir freely. After the addition entire amount of aluminum trichloride, the reaction mixture was allowed to cool to ambient temperature and was stirred overnight. The next morning the reaction mixture was filtered through a sintered glass filter which had been dried at 130 C. The final filtered ionic liquid catalyst was stored under nitrogen in a glass bottle.

Example 1a

Preparation of Trimethylammonium Chloroaluminate Ionic Liquid Catalyst

To a 1000 mL, dry, three neck glass round bottom flask fitted with a mechanical stirrer, thermometer and water cooled reflux condenser was added 67.2 grams (0.7 moles) of trimethylammonium hydrochloride. The hydrochloride salt was heated to 105° C. under vacuum (400 mm Hg) for about 15 hours and then allowed to cool to room temperature under a nitrogen atmosphere. To the hydrochloride salt was added 187.8 grams (1.4 moles) of aluminum trichloride in several portions under nitrogen over about 25 minutes while stirring and increasing the temperature of the flask 135° C. The contents of the flask were then heated to 70° C. and stirred for 1 hour, 45 minutes and then cooled to room temperature under nitrogen. The product, liquid trimethylammonium chloroaluminate ionic liquid, was kept under nitrogen until use.

Example 2

Preparation of Propylene Oligomer

An 800 mL autoclave was purged with nitrogen. 30 mL of the ionic liquid catalyst as prepared in Example 1a and 20 mL of hexane were added to the autoclave by syringe. The autoclave was then evacuated for from about 30 to about 60 seconds to remove the nitrogen in the autoclave. The autoclave was then equilibrated at a temperature of from about 0° C. to about 90° C. while stirring. Propylene gas was added to a pressure of about 50 psig and was maintained at 50 psig over the reaction period. The reaction was run from about 1 hour to about 6 hours. The propylene feed was then disconnected from the autoclave and heating and/or cooling elements were removed. The autoclave was then vented to atmospheric pressure and opened. The hydrocarbon layer was decanted from the ionic liquid catalyst. The ionic liquid catalyst layer was then washed with hexane and the hexane layer was combined with the collected hydrocarbon from the reactor. The hydrocarbon layer was then stirred with water to remove any trace amounts of the ionic liquid catalyst. The hydrocarbon layer was then separated from the water and dried with magnesium sulfate ($MgSO_4$). The propylene oligomer product was isolated from the collected hydrocarbon layer by rotary evaporation taking place at 60° C. to remove any volatile materials.

Example 2a

Oligomerization of Propylene with Ionic Liquid in a Continuous Flow Reactor

A clean, dry, approximately 80 ml glass reactor equipped with a sintered glass frit gas inlet at the bottom and a magnetic stir bar and a needle vent was placed in a water bath heated on a magnetic stirring hot plate and equipped with a thermometer. The reactor was charged with approximately 10 ml of the ionic liquid of Example 1a and then approximately 25 ml of hexane. The water bath was cooled to between 0 and 7° C. with ice and propylene gas was introduced through the gas inlet and allowed to bubble through the ionic liquid at approximately 1.0 liters/minute over approximately 7 hours during which time the water bath was maintained between 40 and 51° C.

The propylene gas flow was stopped and approximately 40 ml of hexane was added to the reactor. The reactor contents were then transferred to a separatory funnel and approximately 10 gms of ice was added to the separatory funnel. The organic layer was washed with water, dried over anhydrous $MgSO4$, filtered and the hexane distilled under vacuum (approximately 20 mm Hg) at approximately 80° C. to afford the oligomerized propylene. This reaction was repeated four times and the oligomerized propylene products from each were combined to yield approximately 260 grams of oligomerized propylene: MWn=769, DI=1.51 by Size Exclusion Chromatography Multi Angle Light Scattering (MALS) analysis.

Example 2b

Oligomerization of Propylene with Ionic Liquid Catalyst in a Continuously Stirred Flow Reactor To a clean, dry, approximately 1 liter, jacketed glass reactor equipped with a bottom drain valve and fitted with a mechanical paddle stirrer, thermometer, fritted glass inlet at the bottom of the reactor and a water cooled condenser fitted with a needle vent was added approximately 130 grams of Ionic Liquid catalyst of Example 1a and approximately 100 ml of hexane. The stirrer was turned on at high speed and the reactor was cooled to between 10-16° C. and propylene gas was introduced through the gas dispersion tube at approximately 1 liter/minute for approximately 1 hour and then lowered to between 0.4-0.6 liters/minute for approximately 7 hours while maintaining the reactor temperature between 23 and 36° C. The propylene flow was stopped, the stirrer stopped and the Ionic Liquid catalyst was drained from the reactor. Approximately 24 hours later, the following day, the Ionic Liquid catalyst was added back to the reactor, the stirrer started and propylene gas was introduced through the gas dispersion tube between 0.4-0.6 liters/minute for approximately 8 hours while maintaining the reactor temperature between 26 and 52° C. The sequence of stopping the propylene gas, draining the Ionic Liquid catalyst and restarting the reaction approximately 24 hours later was repeated twice and then the Ionic Liquid catalyst was drained from the reactor, the organic layer was isolated and washed with water, dried over anhydrous $MgSO4$, filtered and the hexane distilled under vacuum (approximately 20 mm Hg and 80° C.) to afford approximately 500 grams of oligomerized propylene: MWn=917, DI=1.34 by Size Exclusion Chromatography Multi Angle Light Scattering (MALS) analysis.

Example 2c

Oligomerization of Propylene Ionic Liquid Catalyst in a Continuously Stirred Flow Reactor The reactor setup used in Example 2b was used except a slower stirring rate was used and the propylene gas was introduced at between 0.2-0.4 L/minute continuously over approximately 52 hours. The Ionic Liquid catalyst of Example 1a was drained from the reactor, the organic layer was isolated and washed with water, dried over anhydrous MgSO4, filtered and the hexane distilled under vacuum (approximately 20 mm Hg and 80° C.) producing approximately 460 grams of oligomerized propylene: MWn=650, DI=1.37 by Size Exclusion Chromatography Multi Angle Light Scattering (MALS) analysis.

Example 3

Alkylation of Toluene with Oligomerized Propylene with Ionic Liquid Catalyst

To a 100 mL, dry, three neck glass round bottom flask fitted with a mechanical stirrer, thermometer and water cooled reflux condenser was added 17.5 grams (0.189 moles) of toluene followed by 20.0 grams of oligomerized propylene, having a MWn=917 and prepared according to the process of Example 2b, under nitrogen. To this stirring mixture was added approximately 2.0 grams of Methyl-tri-n-butylammonium aluminate ionic liquid, which was prepared according to the process of Example 1a, via syringe at room temperature in one portion. The temperature of the reaction mixture increased to 59° C. within 5 minutes. The reaction product was then poured into approximately 50 grams of ice and washed with water, dried over anhydrous MgSO$_4$, filtered and the excess toluene was distilled under vacuum (approximately 20 mm Hg and 80° C.) to produce a yellow oil. The infrared spectrum of this oil showed weak bands at 705, 727, 756, 783 and 815 cm(−1) which is indicative of multiple substitution on the aromatic ring of toluene and strong bands at 1463 and 1378 cm(−1) which is indicative of polypropylene. Analysis of the product by mass spectroscopy (Time-of-Flight positive mode Field Ionization Mass Spectroscopy with temperature programmed probe inlet −40 to 500° C.) showed the oil to be composed of a mixture of oligomerized propylene toluene alkylates (approximately 95%) by exact mass ranging in molecular weight from about 200 to 900 with the peak molecular weight around 260 and unreacted oligomerized propylene and paraffin (approximately 5%).

Example 4

Alkylation of ortho-xylene with Oligomerized Propylene with Ionic Liquid Catalyst The preparation of an ortho-xylene oligomerized propylene alkylate using an ionic liquid alkylation catalyst was performed in identical fashion to that of Example 3 except 20.1 grams (0.190 moles) of o-xylene was used in place of toluene. The temperature of the reaction increased to 31° C. and the excess o-xylene was removed to produce a yellow oil. The infrared spectrum of this oil showed weak bands at about 817 and 880 cm$^{-1}$ characteristic of 1,2,4 substitution on an aromatic ring and strong bands at 1463 and 1378 cm$^{-1}$ indicative of polypropylene. Analysis of the product by mass spectroscopy (Time-of-Flight positive mode Field Ionization Mass Spectroscopy and temperature programmed probe inlet −40 to 500° C.) showed the oil to be composed of a mixture of oligomerized propylene xylene alkylates (approximately 95%) by exact mass ranging in molecular weight from about 200 to 600 with the peak molecular weight around 330 and unreacted oligomerized propylene and hydrocarbon (approximately 5%).

What is claimed is:

1. A process for alkylating an aromatic compound containing no hydroxyl groups comprising reacting at least one non-hydroxyl containing aromatic compound with at least one olefinic oligomer in the presence of an acidic ionic liquid catalyst, wherein the olefinic oligomer has a carbon range of from about $C_{12}$ to about $C_{70}$ and is synthesized by oligomerizing at least one monoolefin monomer in the presence of an acidic ionic liquid catalyst.

2. The process according to claim 1 wherein the at least one aromatic compound is selected from the group consisting of unsubstituted aromatic compounds, monosubstituted aromatic compounds, and disubstituted aromatic compounds.

3. The process according to claim 2 wherein the at least one aromatic compound is selected from the group consisting of benzene, toluene, meta-xylene, para-xylene, ortho-xylene, and mixtures thereof.

4. The process according to claim 3, wherein the at least one aromatic compound is toluene or ortho-xylene.

5. The process according to claim 1 wherein the olefinic oligomer is selected from the group consisting of a propylene oligomer, a butene oligomer, an isobutylene oligomer, a pentene oligomer, an isopentene oligomer and mixtures thereof.

6. The process according to claim 5 wherein the olefinic oligomer is a propylene oligomer.

7. The process according to claim 1 wherein the acidic ionic liquid catalyst in either the alkylation reaction or the olefin oligomerization independently comprises a first component and a second component, said first component comprising a compound selected from the group consisting of aluminum halide, alkyl aluminum halide, gallium halide, and alkyl gallium halide, and said second component comprising an organic salt or mixtures thereof, wherein said organic salt is selected from the group consisting of an ammonium salt, a phosphonium salt, and a sulfonium salt.

8. The process according to claim 7 wherein the acidic ionic liquid catalyst further comprises a Bronsted acid.

9. The process according to claim 8 wherein the Bronsted acid comprises hydrochloric acid, hydrobromic acid, trifluoromethanesulfonic acid, benzoic acid, para-toluene sulforic acid, or sulfuric acid.

10. The process according to claim 9 wherein the Bronsted acid is hydrochloric acid.

11. The process according to claim 7 wherein the first component is aluminum halide or alkyl aluminum halide.

12. The process according to claim 11 wherein the first component is aluminum trichloride.

13. The process according to claim 7 wherein said second component is selected from the group consisting of a hydrocarbyl substituted ammonium halide, hydrocarbyl substituted imidazolium halide, hydrocarbyl substituted pyridinium halide, alkylene substituted pyridinium dihalide, hydrocarbyl substituted phosphonium halide and mixtures thereof.

14. The process according to claim 13 wherein the second component is an alkyl substituted ammonium halide containing one or more alkyl moieties having from about 1 to about 9 carbon atoms.

15. The process according to claim 14 wherein the second component comprises trimethylamine hydrochloride.

16. The process according to claim 13 wherein the second component is an alkyl substituted imidazolium halide.

17. The process according to claim 16 wherein the second component comprises at least 1-ethyl-3-methyl-imidazolium chloride.

18. The process according to claim 7 wherein the first component is aluminum trichloride and the second component is trimethylammonium hydrochloride.

19. The process according to claim 7 wherein the acidic ionic liquid catalyst in both the alkylation reaction and the olefin oligomerization is the same.

20. The process according to claim 7 wherein the acidic ionic liquid catalyst in the alkylation reaction is different from the acidic ionic liquid catalyst in the olefin oligomerization process.

21. The process according to claim 1 wherein the acidic ionic liquid catalyst in the alkylation reaction is recycled.

22. The process according to claim 1 wherein the alkylation reaction takes place in a continuous process.

* * * * *